United States Patent [19]
Bell et al.

[11] Patent Number: 5,400,529
[45] Date of Patent: * Mar. 28, 1995

[54] SPORTS MEDICINE SHOE

[75] Inventors: Anthony H. G. Bell, Laguna Niguel; Richard D. Ferkel, Van Nuys, both of Calif.

[73] Assignee: Oansh Designs, Ltd., Laguna Niguel, Calif.

[ * ] Notice: The portion of the term of this patent subsequent to Aug. 11, 2009 has been disclaimed.

[21] Appl. No.: 81,654

[22] Filed: Jun. 22, 1993

Related U.S. Application Data

[63] Continuation-in-part of Ser. No. 933,328, Aug. 21, 1992, Pat. No. 5,317,820.

[51] Int. Cl.$^6$ ............................ A43B 7/20; A43B 23/08
[52] U.S. Cl. ............................................. 36/93; 36/89; 36/114; 36/58.5; 36/69
[58] Field of Search ................. 36/89, 90, 114, 58.5, 36/58.6, 69, 140, 29, 153, 71, 100, 93, 50.1, 1.5

[56] References Cited

U.S. PATENT DOCUMENTS

| | | | |
|---|---|---|---|
| 398,892 | 5/1899 | Golden . | |
| 487,492 | 12/1892 | Pugsley . | |
| 518,579 | 4/1894 | Annenberg et al. | 36/2.6 |
| 730,366 | 6/1903 | Gunthrop . | |
| 757,816 | 12/1903 | Kreiger | 36/89 |
| 950,862 | 1/1910 | Nelson . | |
| 1,205,206 | 11/1916 | Hofmeister . | |
| 1,210,255 | 12/1916 | Attschul . | |
| 1,610,700 | 12/1926 | Morton . | |
| 1,692,896 | 2/1923 | Hilgert . | |
| 1,717,432 | 7/1928 | Botti . | |
| 2,302,694 | 11/1942 | Jennings | 36/2.5 |
| 2,729,899 | 1/1956 | Haase | 36/1.5 X |
| 2,774,152 | 12/1956 | Alber | 36/71 |
| 2,800,900 | 7/1957 | Schultz | 128/87 |
| 2,824,390 | 2/1958 | Walker | 36/1.5 |
| 2,830,585 | 4/1958 | Weiss | 36/71 X |
| 2,994,322 | 8/1961 | Cullen et al. | 128/80 |
| 3,138,880 | 1/1963 | Kunzli | 36/2.5 |

(List continued on next page.)

FOREIGN PATENT DOCUMENTS

| | | | |
|---|---|---|---|
| 0040189 | 11/1981 | European Pat. Off. . | |
| 0146208 | 6/1985 | European Pat. Off. . | |
| 0231118 | 7/1987 | European Pat. Off. . | |
| 0350517 | 1/1990 | European Pat. Off. | 36/71 |
| 0521288 | 1/1993 | European Pat. Off. | 36/89 |
| 0014706 | 6/1911 | Germany | 36/1.5 |
| 2637277 | of 1978 | Germany . | |
| 8322899 | 9/1983 | Germany . | |
| 0662483 | 10/1987 | Switzerland . | |
| 9118527 | 12/1991 | WIPO | 36/29 |

OTHER PUBLICATIONS

8 Page brochure by Beuerfeind re: Malleotrain/Malleoloc device.
6 Page brochure featuring Malleoloc Ankle orthosis.

Primary Examiner—Paul T. Sewell
Assistant Examiner—Ted Kavanaugh
Attorney, Agent, or Firm—Stetina Brunda & Buyan

[57] ABSTRACT

An ankle-supporting shoe comprising a sole member having a mid-sole attached to the top surface thereof. Attached to the upper surface of the mid-sole and a toe portion of the top surface of the sole member is a brace member including a base portion formed to suit the shape of the wearer's foot and lateral and medial struts extending upwardly from the base portion. A boot upper is attached to the sole member in a manner wherein the lateral strut extends upwardly within a lateral side panel portion of the boot upper, with the medial strut extending upwardly within a medial side panel portion of the boot upper. An inflatable bladder member is selectively insertable into vamp and ankle portions of the boot upper which is sized and configured to extend about the midfoot ankle and heel of the wearer's foot when the foot is inserted into the boot upper. Lower and intermediate strap members are engaged to the boot upper which, when tightened, cause the lateral and medial struts to assume particular orientations relative the ankle.

37 Claims, 5 Drawing Sheets

U.S. PATENT DOCUMENTS

| | | | |
|---|---|---|---|
| 3,333,353 | 8/1967 | Garcia | 36/69 X |
| 3,584,622 | 6/1971 | Domenico | 128/166 |
| 3,613,273 | 10/1971 | Marquis | 36/2.5 |
| 3,703,775 | 11/1972 | Gatti | 36/50.1 X |
| 3,758,964 | 9/1973 | Nishimura | 36/71 X |
| 4,166,460 | 9/1979 | Applegate | 128/80 |
| 4,255,877 | 3/1981 | Bowerman | 36/129 |
| 4,296,558 | 10/1981 | Antonious | 36/50.1 |
| 4,305,212 | 12/1981 | Coomer | 36/80 |
| 4,342,161 | 8/1982 | Schmohl | 36/114 |
| 4,458,431 | 7/1984 | Sinclair | 36/50.1 X |
| 4,510,701 | 4/1985 | Schour et al. | 36/68 |
| 4,547,981 | 10/1985 | Thais et al. | 36/89 |
| 4,577,419 | 3/1986 | Chassaing | 36/89 |
| 4,676,011 | 6/1987 | O'Rourke et al. | 36/89 |
| 4,719,926 | 1/1988 | Nelson | 128/80 |
| 4,766,681 | 8/1988 | O'Rourke et al. | 36/89 |
| 4,776,111 | 10/1988 | Crowley | 36/89 |
| 4,811,502 | 3/1989 | Sugiyama et al. | 36/127 |
| 4,862,900 | 9/1989 | Hefele | 128/80 |
| 4,864,741 | 9/1989 | Beauchemin | 36/89 |
| 4,912,861 | 4/1990 | Huang | 36/29 |
| 4,958,447 | 9/1990 | Dupree | 36/100 |
| 4,959,912 | 10/1990 | Kaufman et al. | 36/117 |
| 4,989,350 | 2/1991 | Bunch et al. | 36/89 |
| 5,038,762 | 8/1991 | Hess et al. | 128/80 |
| 5,050,598 | 9/1991 | Tucker | 36/2.6 |
| 5,056,509 | 10/1991 | Swearington | 128/80 |
| 5,109,613 | 5/1992 | Van Dyke | 36/89 |
| 5,109,614 | 5/1992 | Curry | 36/100 |
| 5,113,599 | 5/1992 | Cohen et al. | 36/29 |
| 5,131,173 | 7/1992 | Anderie | 36/25 |
| 5,152,082 | 10/1992 | Culpepper | 36/89 |
| 5,175,947 | 1/1993 | Parracho | 36/89 |

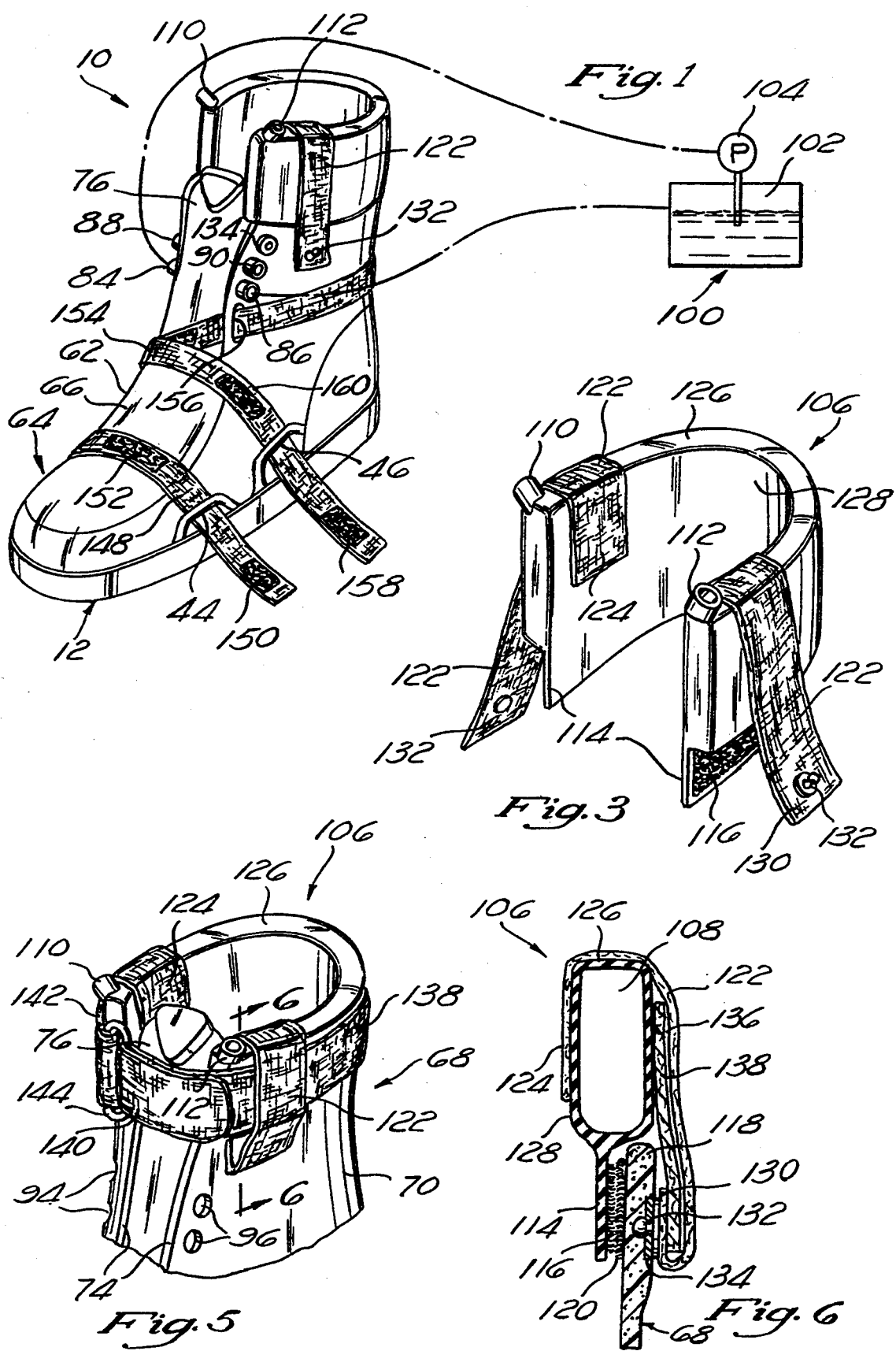

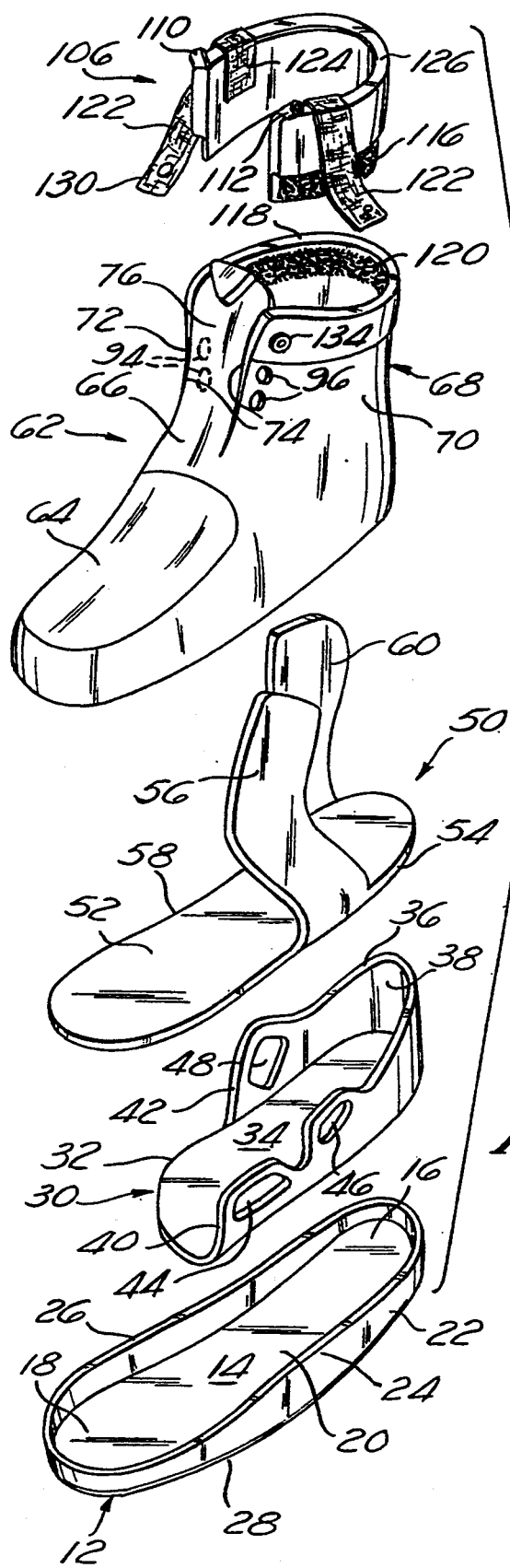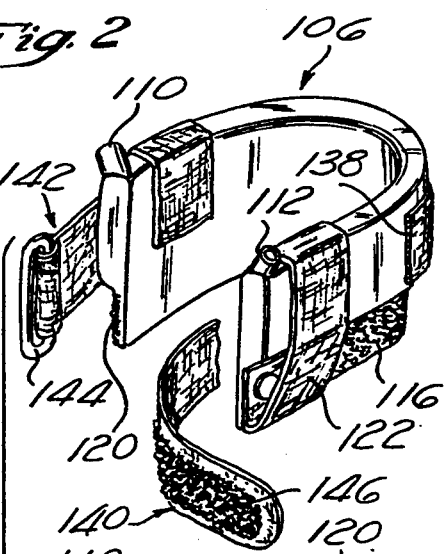

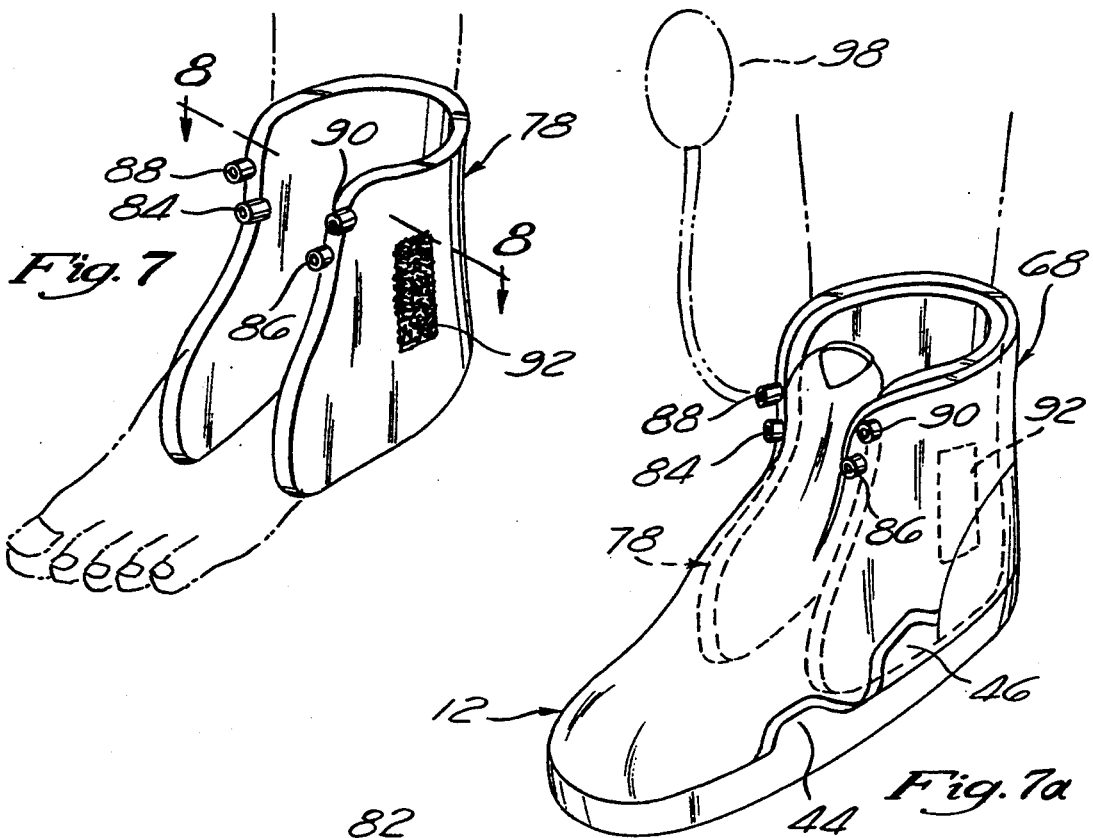
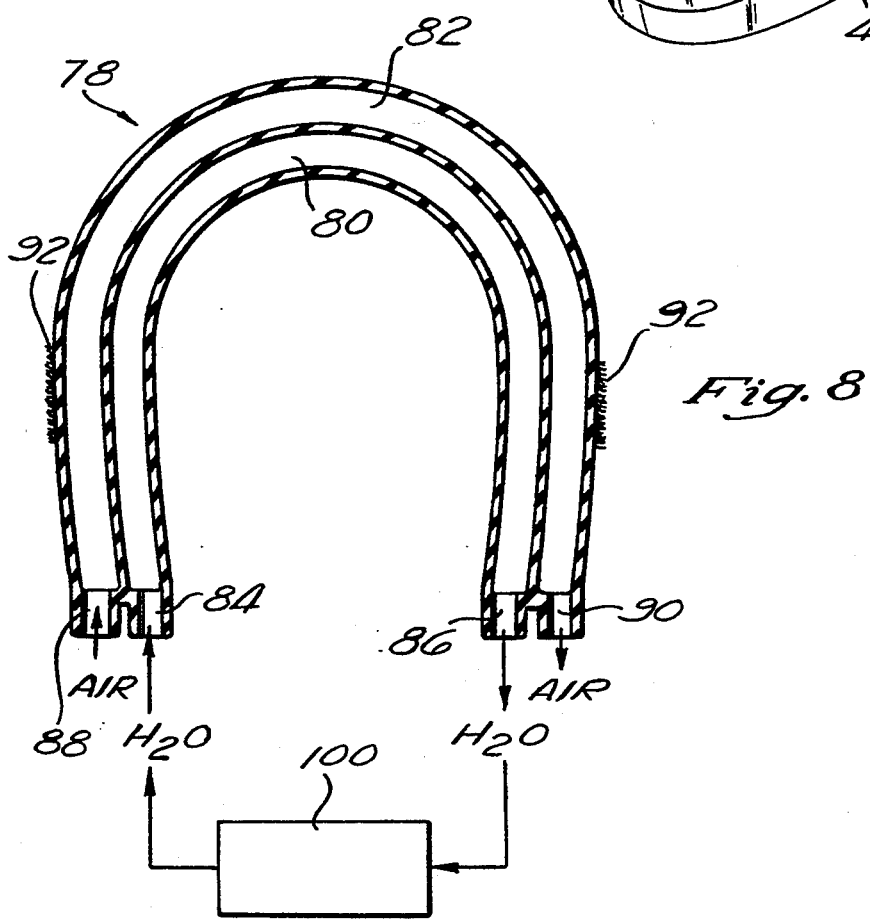

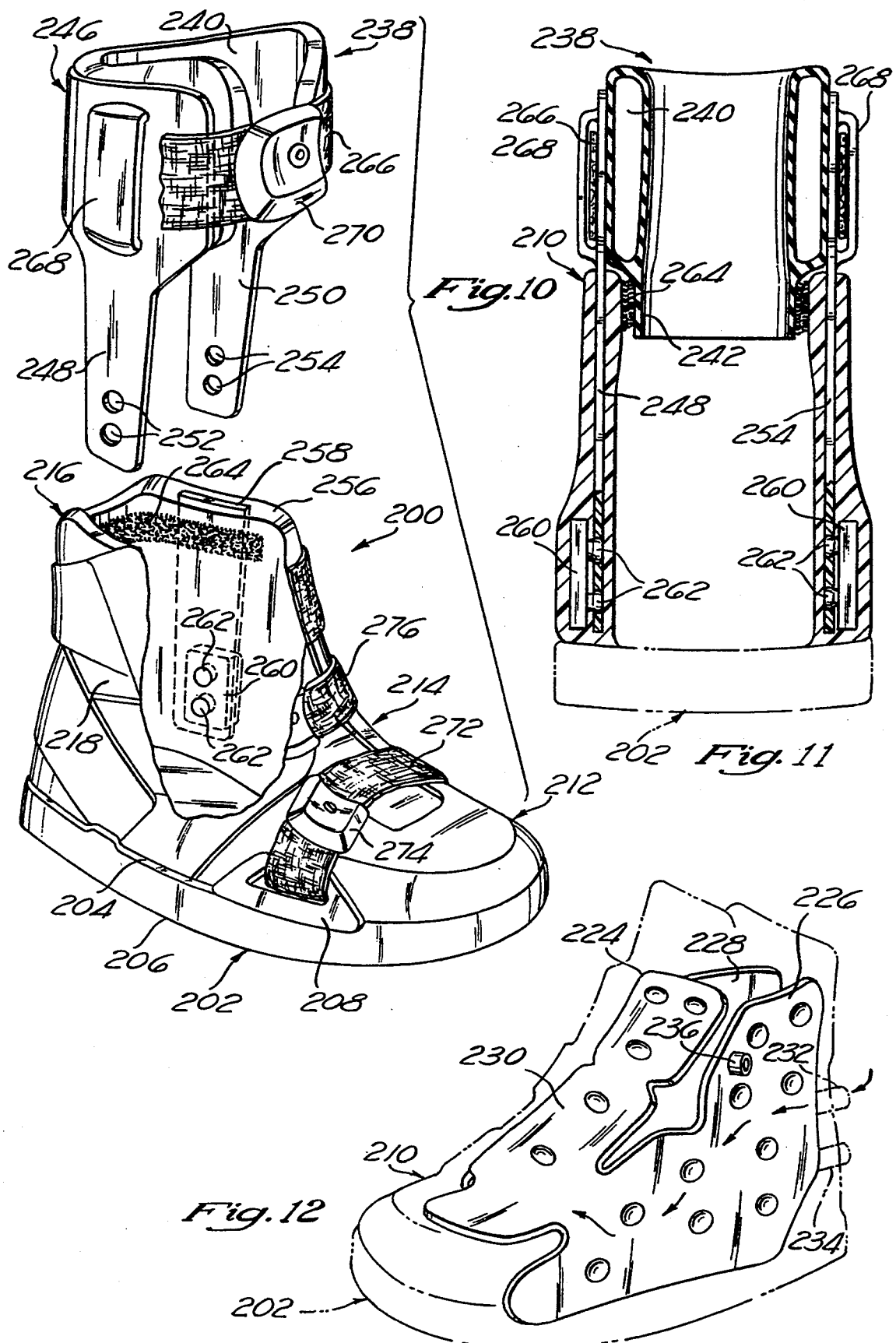

SPORTS MEDICINE SHOE

FIELD OF THE INVENTION

The present application is a continuation-in-part of application Ser. No. 07/933,328, now U.S. Pat. No. 5,417,820, entitled MULTI-APPLICATION ANKLE SUPPORT FOOTWEAR and filed on Aug. 21, 1992, the entire disclosure of which is expressly incorporated herein by reference. The present invention relates generally to footwear, such as shoes, and more particularly to a post-operative shoe for rehabilitating the foot and ankle which is adapted to provide stability to the ankle during the rehabilitation process.

BACKGROUND OF THE INVENTION

Ankle injuries resulting from forced internal rotation and flexion of the ankle joint are commonly seen in work and sport activities and routinely result from participation in sports such as running, tennis, basketball, and hiking. These ankle injuries vary in severity from simple ligament pulls to ligament ruptures and bone fractures. In certain cases, lengthy time periods are required to achieve full recovery, though many types of sprains tend to recur. Additionally, when surgical intervention is required such as an arthroscopic procedure to repair a ligament rupture or the open reduction internal fixation of a fracture, the ankle joint typically exhibits prolonged post-operative swelling which is evident throughout a substantial portion of the rehabilitation process.

In the prior art, a common practice to facilitate the treatment of acute and chronic ankle sprains as well as fractures with minimal displacement of the foot and ankle is to fit the ankle of a patient with a form of a walking cast or brace. Walking casts, braces and other types of post-operative immobilization devices are also commonly utilized subsequent to the aforementioned surgical procedures. An example of a device used to provide rehabilitative support to the ankle joint is disclosed in U.S. Pat. No. 4,771,768 and sold under the trademark Cam Walker II by Zinco Industries, Inc. of Pasadena, Calif. This device generally comprises a boot and strap arrangement which is attachable to the lower leg, ankle and foot of the wearer to provide support to the ankle joint and a selectively adjustable controlled range of ankle motion. However, this device and those similar thereto, as well as walking casts, possess certain deficiencies which detract from their overall utility.

With regard to walking casts, those made of plaster or similar materials are generally susceptible to fatigue cracking and fracture, and typically do not incorporate mechanisms for providing limited movement of the ankle joint. Additionally, since walking casts are not selectively removable from the foot of the patient, hot or cold may not be applied to the ankle joint during the rehabilitation process to facilitate healing. In addition to being bulky and unsightly, walking casts and other types of prior art ankle support devices are also not adapted to reduce the swelling of the ankle during the post-operative rehabilitation process. Further, since walking casts and other types of prior art support devices are fitted to the ankle joint when the same is in a swelled condition, as the swelling is reduced during the rehabilitation process, a poor fit between the walking cast or support device and the wearer's foot often results. Though certain types of prior art ankle support devices are removable from the ankle joint to allow hot or cold to be applied thereto, the inability of these devices to permit such application while the device is in place upon and supporting the ankle joint creates certain risks for the patient. In this respect, when the support device is removed from the foot to treat the ankle joint, the resultant lack of ankle joint support makes the same susceptible to undesired flexion or displacement and further injury. The present invention addresses these and other deficiencies associated with prior art post-operative ankle joint rehabilitation devices by providing a shoe which is adapted to minimize swelling of the ankle joint while providing full support to the same, as well as allow for the application of hot or cold therapy to the ankle joint while the shoe is in place upon the foot of the patient.

SUMMARY OF THE INVENTION

In accordance with the preferred embodiment of the present invention, there is provided a post-operative, ankle supporting, rehabilitative shoe generally comprising a sole member having an outwardly bowed bottom surface and a boot upper attached thereto. The boot upper itself defines a toe portion, a vamp portion and an ankle portion, with the ankle portion surrounding the ankle, heel and lower shin of the wearer's foot and including lateral and medial side panel portions. Attached to the top surface of the sole member is a brace member which includes a base portion formed to suit the shape of and sized to extend substantially along the length of the plantar surface of the wearer's foot. Extending upwardly from the base portion are lateral and medial struts which preferably extend upwardly within the lateral and medial side panel portions of the boot upper when the same is attached to the sole member.

Selectively insertable into the ankle and vamp portions of the boot upper is an inflatable bladder member which is sized and configured to extend about the ankle and heel and over the midfoot of the wearer's foot when the foot is inserted into the shoe. The bladder member defines independently inflatable inner and outer chambers, each of which include inlet and outlet valve ports. The lateral and medial side panel portions of the boot upper include pairs of apertures disposed therein to accommodate the inlet and outlet valve ports of the inner and outer chambers when the bladder member is inserted into the ankle portion. The bladder member also includes at least one Velcro patch attached thereto to maintain the bladder member in releasable engagement to the boot upper when inserted into the ankle portion thereof. A hand-held air pump may be utilized to selectively inflate the outer chamber with air subsequent to the insertion of the bladder member and the wearer's foot into the boot upper, thus providing a compressive force to the ankle joint to minimize the swelling thereof. Further, a portable water pumping apparatus may be utilized to selectively infuse water into the inner chamber subsequent to the insertion of the bladder member and the wearer's foot into the boot upper to provide hot or cold therapy to the ankle joint. Additionally, by coupling the water pumping apparatus to the inlet and outlet valve ports of the inner chamber, hot or cold water may be continuously circulated through the inner chamber of the bladder member while the shoe is in place upon the wearer's foot.

Releasably attachable to the ankle portion of the boot upper is an extension collar for increasing the height of the ankle portion and thus the support provided to the ankle thereby. The extension collar includes a selectively inflatable air bladder therein, as well as an elongate Velcro strip extending thereabout for releasably attaching the same to the ankle portion of the boot upper. The extension collar further includes a pair of stabilization straps attached thereto in opposed relation, each of which are releasably attachable to a respective one of a pair of connector receiving members disposed on a lateral and medial side panel portions of the boot upper. An elongate upper strap may be extended about the extension collar and tightened to maintain the extension collar in tight engagement to the wearer's lower shin.

The shoe constructed in accordance with the present invention further comprises a midsole having a planar portion attached to the top surface of the sole member and disposed between the sole member and the base portion of the brace member. The planar portion is sized to substantially cover the heel and central portions of the top surface and includes a continuous flange formed partially about and extending upwardly therefrom. The flange extends about the heel portion of the top surface and has a first end extending along a lateral edge of the sole member to the toe portion of the top surface and a second end extending along a medial edge of the sole member to a central portion of the top surface. Disposed in side-by-side relation in the first end of the flange are first and second flange apertures while disposed in the second end of the flange is a third flange aperture.

To maintain the shoe upon the wearer's foot, included is an elongate lower strap which extends over the foot portion of the boot and has a first proximal end rigidly secured to the foot portion and a first distal end which extends through the first flange aperture and is releasably attachable to a central portion of the lower strap. Also included is an elongate intermediate strap which extends over the vamp portion of the boot and has a second proximal end rigidly secured to the ankle portion and a second distal end which extends through the third and second apertures, respectively, and is releasably attachable to a central portion of the upper strap. In addition to the foregoing, the shoe comprises at least one insole member which is selectively positionable between the boot upper and the bladder member. The insole member defines a heel cup for receiving the heel of the wearer's foot and is adapted to provide calcaneal support to the heel when the same is received thereinto. Preferably, three insole members are utilized in conjunction with the shoe, each of which includes a decreasing heel cup opening to provide calcaneal support to the foot as the swelling of the ankle joint reduces. When the foot is inserted into the boot upper and the lower and intermediate straps tightened, the lateral strut of the brace member extends about the front of the lateral malleolus of the ankle and upwardly along the lateral and frontal aspects of the ankle, while the medial strut extends behind the medial malleolus of the ankle and upwardly along the medial aspect of the ankle. As such, the lateral and medial struts provide support to the ankle joint alone or in combination with the inflated bladder member. The bladder member may be used to reduce swelling of the ankle joint in addition to providing support thereto, and may also have hot or cold water infused thereinto or circulated therethrough to facilitate desired ankle therapy.

Further in accordance with the present invention, there is provided a method for fabricating a postoperative, ankle supporting, rehabilitative shoe. The preferred method comprises the steps of attaching a mid-sole to a sole member of the shoe. After the mid-sole is attached to the sole member, a brace member is attached to a planar portion of the mid-sole and a portion of the sole member. Thereafter, a boot upper is attached to the sole member in a manner wherein a lateral strut of the brace member extends upwardly within a lateral side panel portion of the boot upper and a medial strut of the brace member extends upwardly within a medial side panel portion of the boot upper. Finally, an inflatable bladder is inserted into the boot upper in a manner wherein the bladder member extends about the ankle and heel and over the midfoot of the wearer's foot when the foot is inserted into the shoe. The preferred method further comprises the steps of inflating an outer chamber of bladder member with air subsequent to the insertion of the bladder member and the wearer's foot into the boot upper, and/or filling an inner chamber of the bladder member with water subsequent to the insertion of the bladder member and the wearer's foot into the boot upper. An additional step includes attaching an extension collar to an ankle portion of the boot upper to increase the total height thereof to provide additional support to the wearer's foot above the ankle joint line.

BRIEF DESCRIPTION OF THE DRAWINGS

These, as well as other features of the present invention, will become more apparent upon reference to the drawings wherein:

FIG. 1 is a lateral side perspective view of the rehabilitative shoe constructed in accordance with the preferred embodiment of the present invention, as interfaced to a water pumping apparatus;

FIG. 2 is an exploded view of certain components comprising the shoe shown in FIG. 1;

FIG. 3 is a perspective view of an extension collar which is releasably attachable to the boot upper of the shoe;

FIG. 4 is an exploded view illustrating the orientation of the extension collar shown in FIG. 3 relative the boot upper of the shoe;

FIG. 5 is a partial lateral perspective view of the shoe illustrating the extension collar engaged thereto;

FIG. 6 is a cross-sectional view taken along line 6—6 of FIG. 5;

FIG. 7 is a perspective view of an inflatable bladder member which is selectively insertable into the boot upper of the shoe;

FIG. 7a is a perspective view illustrating the orientation of the bladder member within the boot upper of the shoe and a hand-held pump used to inflate the bladder member;

FIG. 8 is a cross-sectional view taken along line 8—8 of FIG. 7;

FIG. 10 is an exploded view illustrating the orientation of an alternative embodiment of the extension collar relative the shoe shown in FIG. 9;

FIG. 11 is a rear cross-sectional view of the shoe and extension collar depicted in FIG. 10 as engaged to each other; and FIG. 12 is a perspective view of an alternative embodiment of the inflatable bladder member which is selectively insertable into the boot upper of the shoe depicted in FIG. 9.

DETAILED DESCRIPTION OF THE PREFERRED EMBODIMENTS

Figure 9:
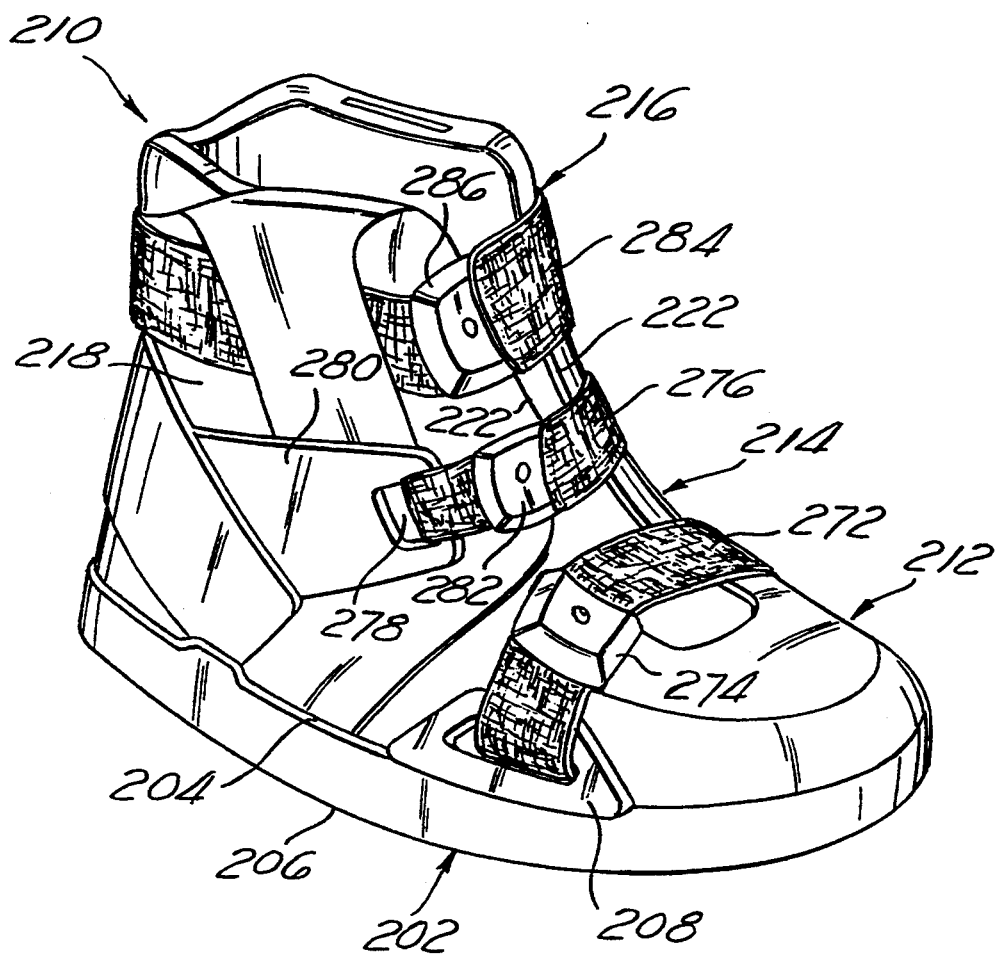
FIG. 9 is a lateral side perspective view of a rehabilitative shoe constructed in accordance with a second embodiment of the present invention.

Referring now to the drawings wherein the showings are for purposes of illustrating a preferred embodiment of the present invention only, and not for purposes of limiting the same, FIG. 1 perspectively illustrates a post-operative, ankle supporting, rehabilitative shoe 10 constructed in accordance with the preferred embodiment of the present invention. The shoe 10 is preferably constructed to resemble an athletic shoe such as a high-top basketball shoe, though it will be recognized that the ankle supporting components of the shoe 10 as will hereinafter described may be incorporated into other types of footwear, such as hiking boots, cross-training shoes, etc.

Referring now to FIGS. 1 and 2, the ankle supporting shoe 10 generally comprises a sole member 12 defining a generally planar top surface 14 having a heel portion 16, a toe portion 18, and a central portion 20 intermediate the heel and toe portions 16, 18. Formed about and extending upwardly from the peripheral edge of the top surface 14 is a continuous wall 22 defining a lateral side 24 and a medial side 26. The sole member 12 further defines a bottom surface 28 having an outwardly bowed configuration, i.e. a "rocker shape". Advantageously, the formation of the bottom surface 28 with the outwardly bowed configuration promotes a smooth, energy conserving gate when the shoe 10 is worn upon the foot of the wearer. In the preferred embodiment, the sole member 12 is fabricated from rubber or a similar material.

Attached to the top surface 14 of the sole member 12 is a mid-sole 30. The mid-sole 30 generally comprises a planar portion 32 which defines an upper surface 34 and is sized to substantially cover the heel portion 16 and central portion 20 of the top surface 14 when attached to the sole member 12. Formed partially about and extending upwardly from the planar portion 32 is a continuous flange 36 defining an inner surface 38, a first end 40, and a second end 42. When the mid-sole 30 is attached to the sole member 12, the flange 36 extends about the heel portion 16 of the top surface 14, with the first end 40 extending along the lateral side 24 of the wall 22 to the toe portion 18 of the top surface 14, and the second end 42 extending along the medial side 26 of the wall 22 to approximately the central portion 20 of the top surface 14. Disposed in the first end 40 of the flange 36 in side-by-side relation are a first aperture 44 and a second aperture 46. Additionally, disposed in the second end 42 of the flange 36 is a third aperture 48. The use of the first, second and third apertures, 44, 46, 48 will be discussed below. Like the sole member 12, the mid-sole 30 is also preferably fabricated from rubber, though other similar materials may be utilized as an alternative.

Attached to the upper surface 34 of the planar portion 32 and to the toe portion 18 of the top surface 14 is a semi-rigid brace member 50. In the preferred embodiment, the brace member 50 generally comprises a base portion 52 which is formed to suit the shape of and is sized to extend substantially Along the entire length of the plantar surface of the wearer's foot. As such, the base portion 52 will completely cover the upper surface 34 of the planar portion 32 and the toe portion 18 of the top surface 14 when attached thereto. Additionally, the base portion 52 has a shape complimentary to the top surface 14 of the sole member 12. However, since the mid-sole 30 is disposed between the top surface 14 and the base portion 52, the base portion 52 is secured directly to the upper surface 34 and only to the toe portion 18 of the top surface 14.

Extending upwardly from the lateral edge 54 of the base portion 52 is a lateral strut 56, while extending upwardly from the medial edge 58 of the base portion 52 is a medial strut 60. As seen in FIG. 2, the lateral and medial struts 56, 60 are oriented such that when the brace member 50 is attached to the mid-sole 30 and sole member 12, the lateral strut 56 will extend upwardly from a position approximately intermediate the heel and central portions 16, 20 of the top surface 14, while the medial strut 60 will extend upwardly from the heel portion 16 of the top surface 14. The use of the lateral and medial struts 56, 60 will be discussed in more detail below. It will be recognized that the mid-sole 30 may be eliminated from the shoe 10 by modifying the configuration of the brace member 50 to include one or more flange portions extending upwardly from the lateral and medial edges 54, 58 of the base portion 52 which define apertures similar to the apertures 44, 46, 48 previously described. Such apertures may also be defined within one or more flange portions extending upwardly from the peripheral edge of the sole member 12.

Attached to the sole member 12 is a boot upper 62. In the preferred embodiment, the boot upper 62 defines a toe portion 64, a vamp portion 66 and an ankle portion 68. The ankle portion 68 itself includes a lateral side panel portion 70 and an opposed medial side panel portion 72 which define inner and outer surfaces, and adjacent edges 74. Extending upwardly between the adjacent edges 74 of the lateral and medial side panel portions 70, 72 is an elongate tongue member 76. As best seen in FIGS. 1 and 2, the boot upper 62 is formed such that the adjacent edges 74 extend only partially along the ankle and vamp portions 68, 66 thereof and do not extend into the toe portion 64. When the wearer's foot is inserted into the boot upper 62, the toes of the foot will reside in the toe portion 64, with the ankle portion 68 surrounding the ankle, heel and lower shin of the wearer's foot. The boot upper 62 is preferably fabricated from a durable, pliable material such as leather, though other materials with similar properties may be utilized as an alternative.

In the preferred embodiment, the boot upper 62 is attached to the sole member 12 in a manner wherein the lateral strut 56 extends upwardly within the lateral side panel portion 70 and the medial strut 60 extends upwardly within the medial side panel portion 72. Alternatively, the boot upper 62 may be attached to the sole member 12 in a manner wherein the lateral strut 56 extends upwardly between the outer surface of the lateral side panel portion 70 and the inner surface 38 of the flange 36, while the medial strut 60 extends upwardly between the outer surface of the medial side panel portion 72 and the inner surface 38 of the flange 36. When the lateral and medial struts 56, 60 are positioned in this manner, the lateral strut 56 is preferably attached to the outer surface of the lateral side panel portion 70, with the medial strut 60 being attached to the outer surface of the medial side panel portion 72. In this respect, the lateral and medial struts 56, 60 are preferably attached to the respective outer surfaces via stitching, though adhesives or other attachment means may also be utilized.

Referring now to FIG. 7, 7a and 8, the shoe 10 constructed in accordance with the present invention further comprises an inflatable bladder member 78 which is selectively insertable into the ankle portion 68 of the boot upper 62. As best seen in FIG. 7, the bladder member 78 is sized and configured to extend about the ankle and heel of the wearer's foot when the foot is inserted into the boot upper 62 of the shoe 10. In the preferred embodiment, the bladder member 78 is fabricated from rubber on a like expandable material and defines an inner chamber 80 and an outer chamber 82, each of which are independently inflatable. In this respect, fluidly coupled to the inner chamber 80 are an inlet valve port 84 and an outlet valve port 86, while fluidly coupled to the outer chamber 82 are an inlet valve port 88 and an outlet valve port 90. To maintain the bladder member 78 in releasable engagement to the boot upper 62 when inserted into the ankle portion 68 thereof, attached to the lateral and medial outer surface portions of the bladder member 78 in opposed relation are a pair of Velcro patches 92. The Velcro patches 92 are releasably engaged to the inner surfaces of the lateral and medial side panel portions 70, 72 of the boot upper 62 when inserted into the ankle portion 68, thus maintaining the bladder member 78 in a proper orientation relative the wearer's foot when the same is inserted into the shoe 10.

As best seen in FIGS. 1, 5 and 7a, disposed within the lateral and medial side panel portions 70, 72 of the boot upper 62 in close proximity to the adjacent edges 74 thereof, are a first pair of apertures 94 and a second pair of apertures 96. When the bladder member 78 is inserted into the ankle portion 68 of the boot upper 62, the first pair of apertures 94 are adapted to accommodate the inlet valve ports 84, 88 of the inner and outer chambers 80, 82, while the second pair of apertures 96 are adapted to accommodate the outlet valve ports 86, 90 of the inner and outer chambers 80, 82. In this respect, the inlet valve ports 84, 88 and outlet valve ports 86, 90 are extended through respective apertures of the first and second pairs 94, 96 such that the distal ends thereof protrude slightly outwardly from the boot upper 62, as best seen in FIG. 1.

In the preferred embodiment, the outer chamber 82 of the bladder member 78 is typically inflated with air subsequent to the insertion of the bladder member 78 and the wearer's foot into the boot upper 62. In this respect, the inflation of the outer chamber 82 with air is preferably accomplished via the utilization of a hand-held pump 98 which is fluidly connectable to the inlet valve port 88 of the outer chamber 82. Advantageously, the inflation of the outer chamber 82 of the bladder member 78 with air subsequent to the insertion of the foot into the boot upper 62 causes the bladder member 78 to exert compressive pressure on the ankle joint of the foot thus minimizing swelling and pain. Additionally, as the swelling of the ankle reduces during the post-operative rehabilitation process, the outer chamber 82 may be inflated to create a snug fit between the shoe 10 and the wearer's foot by filling any excess space between the shoe 10 and the wearer's foot caused by the reduced swelling of the ankle. The outer chamber 82 is deflated by opening the outlet valve port 90.

Referring now to FIGS. 1 and 8, the inner chamber 80 of the bladder member 78 is preferably filled with hot or cold water subsequent to the insertion of the bladder member 78 and wearer's foot into the boot upper 62 of the shoe 10. Hot or cold water may be infused into the inner chamber 80 via a water pumping apparatus 100 which is fluidly connectable to the inlet valve port 84.

The water pumping apparatus 100 preferably comprises an insulated water retaining basin 102 and an associated fluid pump 104. When it is desired to infuse hot or cold water into the inner chamber 80, the water pumping apparatus 100, and more particularly the pump 104, is fluidly coupled to the inlet valve port 84 and activated, thus causing the hot or cold water within the basin 102 to be pumped into the inner chamber 80. The water is drained from the inner chamber 80 by removing the bladder member 78 from within the boot upper 62 and opening the outlet valve port 86. As will be recognized, the inner chamber 80 rather than the outer chamber 82 is filled with the hot or cold water since it is disposed in closest proximity, i.e. applied directly to, the wearer's ankle when the bladder member 78 is properly positioned within the boot upper 62 and the wearer's foot inserted thereinto. Typically, the bladder member 78 maintains the desired temperature of the hot or cold water infused into the inner chamber 80 thereof for a period of up to eight hours before replacement of the water is necessitated due to heating or cooling.

In addition to being adapted to infuse water into the inner chamber 80, the water pumping apparatus 100 is further adapted to circulate hot or cold water through the inner chamber 80 in the manner depicted in FIGS. 1 and 8. In this respect, the pump 104 may be fluidly coupled to the inlet valve port 84, with the outlet valve port 86 being fluidly coupled to the basin 102. Thereafter, the activation of the pump 104 circulates the hot or cold water through the inner chamber 80 of the bladder member 78. When cold water is circulated through the bladder member 78, a thermostat included in the water pumping apparatus 100 will deactivate the pump 104 when the water temperature drops below forty (40) degrees Fahrenheit. As previously specified, the water retaining basin 102 of the water pumping apparatus 100 is insulated to maintain the temperature of the water therewithin at a desired level. The pumping apparatus 100 also includes a standard 12-volt plug to power the pump 104. As will be recognized, the ability to circulate hot or cold water through the bladder member 78 via the water pumping apparatus 100 allows for the therapeutic treatment of the ankle without the necessity of having to remove the shoe 10 from the wearer's foot. The infusion of water into or circulation of water through the inner chamber 80 may occur exclusively or in combination with the inflation of the outer chamber 82 with air through the utilization of the hand-held pump 98.

Referring now to FIGS. 1-6, the rehabilitative shoe 10 of the present invention further comprises an extension collar 106 which is releasably attachable to the ankle portion 68 of the boot upper 62 for increasing the height of the ankle portion 68 and the support provided to the ankle joint thereby. The extension collar 106 has a generally U-shaped configuration and comprises an inflatable bladder 108 which is preferably covered with a pliable material such as cloth or leather. Similar to the bladder member 78 previously described, the inflatable bladder 108 of the extension collar 106 includes an inlet valve port 110 and an outlet valve port 112 for selectively inflating and deflating the bladder 108 with air. In this respect, the hand-held pump 98 utilized to inflate the outer chamber 82 of the bladder member 78 with air may also be utilized to inflate the bladder 108 of the extension collar 106 with air by coupling the same to the inlet valve port 110. The bladder 108 is deflated by opening the outlet valve port 112. As best seen in FIG.

6, the bladder member 108 is formed in a manner defining a downwardly extending wall portion 114 which includes an elongate Velcro strip 116 attached thereto and extending about the outer surface thereof.

The extension collar 106 is releasably attached to the upper rim or cuff 118 of the ankle portion 68 defining the entrance to the boot upper 62. In the preferred embodiment, this releasable attachment is facilitated by the engagement of the Velcro strip 116 to a corresponding Velcro strip 120 attached to and extending about the interior of the ankle portion 68 immediately below the cuff 118 thereof. In addition to the engagement of the Velcro strips 116, 120 to each other, the releasable attachment of the extension collar 106 to the ankle portion 68 is further accomplished through the engagement of a pair of elongate stabilization straps 122 of the extension collar 106 to the ankle portion 68. In the preferred embodiment, the stabilization straps 122 are attached to respective ends of the extension collar 106 in opposed relation, and include upper ends 124 which are wrapped over the top edge 126 of the inflatable bladder 108 and rigidly secured to the inner surface 128 thereof. The stabilization straps 122 further include lower ends 130,- each of which include a snap connector 132 attached to the outer surface thereof. Subsequent to the engagement of the Velcro strip 116 to the Velcro strip 120, the lower ends 130 of the stabilization straps 122 are bent inwardly and upwardly so as to facilitate the releasable receipt of the snap connectors 132 into corresponding connector receiving members 134 attached to the lateral and medial side panel portions 70, 72 of the ankle portion 68 in close proximity to the adjacent edges 74 thereof. Each of the stabilization straps 122 is fabricated from a pliable material such as cloth or leather, and includes a reinforcement member 136 attached to the inner surface thereof intermediate the upper and lower ends 124, 130 which extends along the outer surface of the inflatable bladder 108 and over the cuff 118.

When the extension collar 106 is attached to the ankle portion 68 of the boot upper 62, the overall height of the shoe 10 is increased to approximately 10 inches, thus providing added support to the wearer's foot above the joint line of the ankle when the bladder 108 is inflated with air via the utilization of the hand-held pump 98. Once a determination is made that the extra stability afforded by the attachment of the extension collar 106 to the ankle portion 68 is no longer required, the same may be easily removed by unsnapping the snap connectors 132 from within the connector receiving members 134 and peeling the Velcro strip 120 out of engagement to the Velcro strip 118.

When the extension collar 106 is inflated and attached to the ankle portion 68, the snug engagement thereof to the lower shin portion of the wearer's foot is facilitated by an elongate upper strap 138 which is extensible about the extension collar 106, and more particularly the outer surface of the inflatable bladder 108. As best seen in FIGS. 4 and 6, the upper strap 138 includes a central portion which is rigidly affixed to the outer surface of the inflatable bladder 108, a proximal end 140 which extends forwardly from one end of the inflatable bladder 108, and a distal end 142 which extends forwardly from the opposite end of the inflatable bladder 108 and includes a loop connector 144 attached thereto. The extension collar 106 is tightened about the lower shin of the foot by extending the proximal end 140 through the loop connector 144 disposed on the distal end 142, and pulling the same sufficiently to tighten the extension collar 106 about the lower shin. Thereafter, the proximal end 140 of the upper strap 138 is releasably secured to a proximal portion of the upper strap 138 via a Velcro patch 146 disposed thereon. As seen in FIG. 6, when the upper strap 138 is tightened and the stabilization straps 122 attached to the ankle portion 68, the upper strap 138 will extend between the outer surface of the inflatable bladder 108 and the reinforcement members 136 attached to the inner surfaces of the stabilization straps 122. Additionally, as seen in FIG. 5, the inflatable bladder 108 is configured in a manner wherein the same substantially overlaps the cuff 118 of the ankle portion 68 when the extension collar 106 is engaged thereto.

Though not shown, the shoe 10 may further include one to three insole members which are selectively positionable between the boot upper 62 and the bladder member 78. Each insole member defines a heel cup for receiving the heel of the wearer's foot and is adapted to provide calcaneal support to the foot. In this respect, the three insole members preferably utilized in association with the shoe 10 each include heel cups of decreasing size to provide the necessary calcaneal support as the swelling of the ankle reduces during the rehabilitation process.

Referring now to FIG. 1, the shoe 10 of the present invention further comprises a pair of selectively tightenable fastening straps which are cooperatively engaged to the boot upper 62 and operable to compress the boot upper 62 when tightened to maintain the shoe 10 upon the wearer's foot. In the preferred embodiment, the shoe 10 includes an elongate lower strap 148 which extends over the toe portion 64 of the boot upper 62 and includes a proximal end rigidly secured to the medial side of the toe portion 64 and a distal end which is extended through the first aperture 44 of the mid-sole 30 and releasably secured to a central portion of the lower strap 148 via a Velcro patch 150 thereon which is engageable to a Velcro patch 152 attached to a central portion of the lower strap 148.

In addition to the lower strap 148, the shoe 10 includes an elongate intermediate strap 154 which extends over the vamp portion 66 of the boot upper 62. The intermediate strap 154 defines a proximal end which is rigidly secured to the ankle portion 68 of the boot upper 62, and a distal end which is extended through an elongate opening 156 disposed in the lateral side panel portion 70, and through the third and second apertures 48, 46 of the midsole 30, respectively. After being tightened, a Velcro patch 158 disposed on the distal end of the intermediate strap 154 is releasably secured to a Velcro patch 160 disposed on a central portion of the intermediate strap 154.

When the foot of the wearer is inserted into the boot upper 62 of the shoe 10 and rested upon the base portion 52 of the brace member 50, the tightening of the lower and intermediate straps 148, 154 causes the lateral and the medial struts 56, 60 of the brace member 50 to assume particular orientations relative the ankle of the wearer's foot. Particularly, the lateral strut 56 is formed and oriented on the lateral edge 54 of the base portion 52 so as to extend about the front of the lateral malleolus of the ankle and upwardly along the lateral and frontal aspects of the ankle. Additionally, the medial strut 60 is formed and oriented on the medial edge 58 of the base portion 52 so as to extend behind the medial malleolus of the ankle and upwardly along the medial aspect of the ankle. The tightening of the lower and intermediate straps 148, 154 further serves to compress the boot upper 62 which causes the adjacent edges 74 of the lateral and medial side panel portions 70, 72 to draw toward each other, thus maintaining the shoe 10 upon the foot of the wearer. Advantageously, the aforementioned positioning of the lateral and medial struts 56, 60 provides support to the ankle of the wearer in a manner adapted to prevent injury thereto during the ankle rehabilitation process. Though the brace member 50 prevents the twisting or inversion of the ankle, it permits normal flexion of the ankle to occur, thus not excessively restricting the ankle's movement. The brace member 50 is preferably fabricated from a semi-rigid plastic material possessing sufficient resiliency so as to allow the lateral and medial struts 56, 60 to be manipulated via the lower and intermediate straps 148, 154 to their desired orientations relative the lateral malleolus and medial malleolus of the ankle. Importantly, the pliable nature of the leather material preferably utilized to fabricate the boot upper 62 allows the lateral and medial struts 56, 60 to be manipulated to the proper orientations despite being extended upwardly within the lateral and medial side panel portions 70, 72 of the boot upper 62.

The shoe 10 of the present invention is preferably fabricated by first attaching the mid-sole 30 to the top surface 14 of the sole member 12 in the aforementioned manner. Thereafter, the brace member 50 is attached to the upper surface 34 of the planar portion 32 as well as the toe portion 18 of the top surface 14. When attached to the upper surface 34 and the top surface 14, the brace member 50 is oriented such that the lateral strut 56 extends upwardly from the lateral side 24 of the sole member 12, with the medial strut 60 extending upwardly from the medial side 26 of the sole member 12. Additionally, the mid-sole 30 is attached to the sole member 12 such that the first end 40 of the flange 36 extends along the lateral side 24, with the second end 42 of the flange 36 extending along the medial side 26.

After the mid-sole 30 and the brace member 50 have been secured to the sole member 12, the boot upper 62 is attached thereto in the aforementioned manner such that the lateral and medial struts 56, 60 extend upwardly within the lateral and medial side panel portions 70, 72. Thereafter, the inflatable bladder member 78 is inserted into the boot upper 62 in a manner wherein the bladder member 78 extends about the ankle and heel of the wearer's foot when the foot is inserted into the boot upper 62. The preferred method of fabricating the boot may further comprise the step of inflating the outer chamber 82 of the bladder member 78 with air subsequent to the insertion of the bladder member 78 and the wearer's foot into the boot upper 62, and/or the step of filling the inner chamber 80 with hot or cold water or circulating water therethrough. Additionally, the steps of attaching the extension collar 106 to the ankle portion 68 of the boot upper 62 and/or selectively inserting insole members into the ankle portion 68 may also be included.

Typically, the shoe 10 will be provided to the wearer with the extension collar 106 already engaged to the ankle portion 68 of the boot upper 62 and the bladder member 78 positioned therein. However, there will be no air within the inflatable bladder 108 and no air or water within the inner and outer chambers 80, 82 of the bladder member 78. The wearer's foot will be inserted into the boot upper 62 by folding away the tongue member 76. Once the foot is properly positioned within the shoe 10, the tightening of the lower and intermediate straps 148, 154 will immediately cause the lateral and medial struts 56, 60 of the brace member 50 to provide support to the ankle. Typically, the lower strap 148 will be tightened first, followed by the tightening of the intermediate strap 154. Thereafter, the upper strap 138 extending about the extension collar 106 will be tightened to provide a snug fit between the extension collar 106 and the lower shin area of the wearer's foot. The hand-held pump 98 is then utilized to inflate the bladder 108 of the extension collar 106 and the outer chamber 82 of the bladder member 78. In addition or as an alternative to inflating the outer chamber 82 with air, the inner chamber 80 of the bladder member 78 may be filled with hot or cold water or attached to the water pumping apparatus 100 in the aforementioned manner to circulate hot or cold water therethrough.

Advantageously, the shoe 10 provides the wearer with enhanced comfort and mobility, and facilitates a reduction in pain and swelling due to the compressive forces exerted against the ankle joint by the inflation of the inner chamber 80 with air. Since hot or cold water may be circulated through the inner chamber 80, the ankle may be therapeutically treated without the necessity of having to remove the shoe 10 from the wearer's foot. Typically, when the water pumping apparatus 100 is utilized to circulate hot or cold water through the inner chamber 80, the outer chamber 82 is deflated, and is reinflated with air subsequent to the completion of the water circulation treatment. Once a determination is made that the extra support provided by the extension collar 106 is no longer necessary, the same may be removed from the ankle portion 68 of the boot upper 62. Further, as the swelling of the ankle joint is reduced, the inflation of the outer chamber 82 will aid in maintaining a snug fit between the shoe 10 and wearer's foot by filling in the excess space in the shoe 10 created by the reduction in swelling. The insole members will also help improve the fit of the shoe 10 upon the foot when the swelling reduces around the calcaneal. During the latter stages of the rehabilitation period, the lateral and medial struts 56, 60 of the brace member 50 will themselves provide the necessary support for the ankle. As such, the shoe 10 allows a patient to rehabilitate an injured ankle at home or in the office without the necessity of having to visit a physician or hospital, and permits increased mobility while facilitating easy and immediate rehabilitation for most foot and ankle injuries.

Referring now to FIG. 9, perspectively illustrated is a post-operative, ankle supporting, rehabilitative shoe 200 constructed in accordance with a second embodiment of the present invention. The shoe 200 comprises a sole member 202 which is similarly configured to the previously described sole member 12, and defines a generally planar top surface having heel and toe portions, as well as a central portion intermediate the heel and toe portions. The sole member 202 further defines a continuous wall formed about and extending upwardly from the peripheral edge of the top surface thereof which itself defines a lateral side 204 and a medial side. Like the sole member 12, the bottom surface 206 of the sole member 202 has an outwardly bowed configuration or "rocker shape" to promote a smooth, energy conserving gate when the shoe 200 is worn upon the foot of the wearer. Attached to the lateral side 204 of the wall member along the toe portion of the top surface is a first loop member 208, the use of which will be discussed below.

In the second embodiment, the shoe 200 does not include a mid-sole attached to the top surface of the sole member 202. However, though not shown, attached to the top surface of the sole member 202 is a semi-rigid brace member which is identically configured to the brace member 50 previously described in relation to the shoe 10.

In addition to the brace member, attached to the sole member 202 is a boot upper 210. In the second embodiment, the boot upper 210 defines a toe portion 212, a vamp portion 214 and an ankle portion 216. The ankle portion 216 itself includes a lateral side panel portion 218 and an opposed medial side panel portion 220 which define inner and outer surfaces, and adjacent edges 222. Though not shown, extending upwardly between the adjacent edges 222 of the lateral and medial side panel portions 218, 220 is an elongate tongue member. Like the previously described shoe 10, the boot upper 210 is formed such that the adjacent edges 222 extend only partially along the ankle and vamp portions 216, 214 thereof and do not extend into the toe portion 212. As such, when the wearer's foot is inserted into the boot upper 210, the toes of the foot will reside in the toe portion 212, with the ankle portion 216 surrounding the ankle, heel and lower shin of the wearer's foot and the vamp portion 214 overlying the midfoot. The boot upper 210 is fabricated from a durable, pliable material such as leather, though other materials with similar properties may also be utilized. The boot upper 210 is attached to the sole member 202 in a manner wherein the lateral strut of the brace member attached to the top surface of the sole member 202 extends upwardly within the lateral side panel portion 218 and the medial strut of the brace member extends upwardly within the medial side panel portion 220.

Referring now to FIG. 12, selectively insertable into the ankle and vamp portions 216, 214 of the boot upper 210 is an inflatable bladder member 224. In the second embodiment, the bladder member 224 defines a lateral portion 226, a medial portion 228 and a vamp portion 230 which are fluidly coupled to each other. The bladder member 224 is sized and configured to extend about the ankle and heel of the wearer's foot, as well as over the midfoot, when the foot is inserted into the boot upper 210 of the shoe 200. Particularly, the lateral and medial portions 226, 228 extend along the lateral and medial sides of the wearer's foot and are wrapped about the ankle and heel portions thereof. The vamp portion 230 which extends between the front ends of the lateral and medial portions 226, 228 lies over and substantially covers the midfoot. Like the bladder member 78 previously described in relation to the shoe 10, the bladder member 224 is fabricated from rubber or a like expandable material and defines an inner chamber and an outer chamber, each of which are independently inflatable. Fluidly coupled to the inner chamber of the bladder member 224 are an inlet valve port 232 and an outlet valve port 234, while fluidly coupled to the outer chamber is an inlet/outlet valve port 236. In the second embodiment, the inlet and outlet valve ports 232, 234, are disposed in vertical alignment and extend rearwardly from the back end of the bladder member 224 which wraps about the heel of the wearer's foot. The inlet/outlet valve port 236 preferably extends outwardly from the upper region of the lateral portion 226.

Though not shown, disposed within the lateral side panel portion 218 of the boot upper 210 in close proximity to the adjacent edge 222 thereof is an aperture which is adapted to accommodate the inlet/outlet valve port 236 of the bladder member 224 when the same is inserted into the boot upper 210. In this respect, the inlet/outlet valve port 236 is extended through the aperture disposed within the lateral side panel portion 218 such that the distal end thereof protrudes slightly outwardly from the boot upper 210. Additionally, disposed within the rear or heel portion of the boot upper 210 in close proximity to the wall of the sole member 202 are a pair of vertically aligned apertures,. When the bladder member 224 is inserted into the boot upper 210, the vertically aligned apertures are adapted to accommodate the vertically aligned inlet and outlet valve ports 232, 234 of the bladder member 224. In this respect, the inlet and outlet valve ports 232, 234 are extended through respective apertures of the pair such that the distal ends thereof protrude slightly outwardly from the heel region of the boot upper 210, as best seen in FIG. 12.

In the second embodiment, the outer chamber of the bladder member 224 is typically inflated with air subsequent to the insertion of the bladder member 224 and the wearer's foot into the boot upper 210. The inflation of the outer chamber with air is preferably accomplished via the utilization of the hand-held pump 98 depicted in FIG. 7(a) which is fluidly connectable to the inlet/outlet valve port 236 of the outer chamber. As with the bladder member 78, the inflation of the outer chamber of the bladder member 224 with air subsequent to the insertion of the foot into the boot upper 210 causes the bladder member 224 to exert compressive pressure on the ankle and midfoot of the wearer, and particularly the ankle joint, thus minimizing swelling and pain. Additionally, as the swelling of the ankle reduces during the post-operative rehabilitation process, the outer chamber may be inflated to create a snug fit between the shoe 200 and the wearer's foot by filling any excess space between the shoe 200 and the wearer's foot caused by the reduced swelling of the ankle.

The inner chamber of the bladder member 224 may also be filled with hot or cold water subsequent to the insertion of the bladder member 224 and wearer's foot into the boot upper 210 of the shoe 200. Particularly, hot or cold water may be infused into the inner chamber via the previously described water pumping apparatus 100 which is fluidly connectable to the inlet valve port 232. When the hot or cold water is infused into the inlet valve port 232, the water flows in the direction depicted by the arrows in FIG. 12, and thus completely fills the lateral, medial and vamp portions 226, 228, 230 of the bladder member 224. The water is drained from the inner chamber via the outlet valve port 234. The inner chamber is filled with the hot or cold water since, as in the bladder member 78, it is disposed in closest proximity, i.e. applied directly to, the wearer's foot and ankle when the bladder member 224 is properly positioned within the boot upper 210 and the wearer's foot inserted thereinto. The bladder member 224 also maintains the desired temperature of the hot or cold water infused into the inner chamber thereof for a period of up to eight hours before replacement of the water is necessitated due to heating or cooling.

The water pumping apparatus 100 may also be utilized to circulate hot or cold water through the inner chamber of the inflatable bladder member 224. In this respect, the pump 104 of the water pumping apparatus 100 may be fluidly coupled to the inlet valve port 232, with the outlet valve port 234 being fluidly coupled to the basin 102 thereof. Thereafter, the activation of the pump 104 circulates the hot or cold water through the inner chamber of the bladder member 224. The ability to circulate hot or cold water through the bladder member 224 via the water pumping apparatus 100 allows for the therapeutic treatment of the ankle without the necessity of having to remove the shoe 200 from the wearer's foot. The infusion of water into or circulation of water through the inner chamber of the bladder member 224 may occur exclusively or in combination with the inflation of the outer chamber with air through the utilization of the hand-held pump 98.

Referring now to FIGS. 10 and 11, the rehabilitative shoe 200 further comprises an extension collar 238 which is releasably attachable to the ankle portion 216 of the boot upper 210 for increasing the height of the ankle portion 216 and the support provided to the ankle joint thereby. In the second embodiment, the extension collar 238 comprises an inflatable bladder 240 which has a generally U-shaped configuration and is preferably covered with a pliable material such as cloth or leather. Though not shown, the inflatable bladder 240 includes an inlet/outlet valve-port for selectively inflating and deflating the bladder 240 with air. In this respect, the hand-held pump 98 utilized to inflate the outer chamber of the bladder member 224 with air may also be utilized to inflate the bladder 240 with air by coupling the same to the inlet/outlet valve port thereof. As best seen in FIG. 11, the bladder 240 is formed in a manner defining a downwardly extending wall portion 242 which includes an elongate Velcro strip 244 attached thereto and extending about the outer surface thereof.

In the second embodiment, the outer surface of the bladder 240 is secured to the arcuately contoured inner surface of a rigid, generally U-shaped support member 246. The support member 246 defines an elongate lateral strut 248 and an elongate medial strut 250 which extend downwardly in opposed relation. Disposed in the lateral strut 248 adjacent the distal end thereof is a first pair of vertically aligned apertures 252, while disposed in the medial strut 250 adjacent the distal end thereof is a second pair of vertically aligned apertures 254, each of which are axially aligned with a respective one of the apertures 252 of the first pair.

The extension collar 238 is releasably attached to the upper rim or cuff 256 of the ankle portion 216 defining the entrance to the boot upper 210. This releasable attachment is facilitated by the receipt of the lateral and medial struts 248, 250 into a corresponding pair of elongate slots 258 disposed within the cuff 256 of the boot upper 210. The lateral and medial struts 248, 250 are lowered through the slots 258 until such time as the downwardly extending wall 242 of the bladder 240 is completely received into the ankle portion 216 of the boot upper 210, i.e. the cuff 256 is abutted against the bladder 240. As will be recognized, when the extension collar 238 is positioned in this manner, the lateral and medial struts 248, 250 are fully received into the lateral and medial side panel portions 218, 220, respectively, of the boot upper 210. Disposed within the lateral and medial side panel portions 218, 220 in opposed relation are a pair of identically configured connector members 260, each of which define a pair of vertically aligned, cylindrically configured projections 262 extending inwardly therefrom. When the lateral and medial struts 248, 250 are fully received into the lateral and medial side panel portions 218, 220, the projections 262 of the connector member 260 disposed within the lateral side panel portion 218 are received, i.e. snapped into, the first pair of apertures 252 disposed within the lateral strut 248. Similarly, the projections 262 of the connector member 260 disposed within the medial side panel portion 220 are received into the second pair of apertures 254 disposed within the medial strut 250. Importantly, the receipt of the projections 262 of the connector members 260 into the lateral and medial struts 248, 250 maintains the extension collar 238 in rigid engagement to the boot upper 210. In addition to the engagement of the lateral and medial struts 248, 250 to the connector members 260, the releasable attachment of the extension collar 238 to the ankle portion 216 is further accomplished by the engagement of the Velcro strip 244 to a corresponding Velcro strip 264 attached to and extending about the interior of the ankle portion 216 immediately below the cuff 256 thereof.

When the extension collar 238 is attached to the ankle portion 216 of the boot upper 210, the overall height of the shoe 200 is increased to approximately ten inches, thus providing added support to the wearer's foot above the joint line of the ankle when the bladder 240 is inflated with air via the utilization of the hand-held pump 98. Once a determination is made that the extra stability afforded by the attachment of the extension collar 238 to the ankle portion 216 is no longer required, the same may be easily removed by unsnapping the connector members 260 from the lateral and medial struts 248, 250 and peeling the Velcro strip 244 out of engagement to the Velcro strip 264.

When the extension collar 238 is inflated and attached to the ankle portion 216, the snug engagement thereof to the lower shin portion of the wearer's foot is facilitated by an elongate collar strap 266 which is extensible about the extension collar 238, and more particularly the outer surface of the support member 246. As seen in FIGS. 10 and 11, the opposed ends of the collar strap 266 are extended through a pair of sleeves 268 formed on the outer surface of the support member 246 in opposed relation, and are secured to one another via a fastening member 270. When the collar'strap 266 is tightened, the opposed ends of the U-shaped support member 246 and bladder 240 are drawn toward each other, thus tightening the extension collar 238 about the lower shin.

Like the shoe 10, the shoe 200 may include one to three insole members which are selectively positionable between the boot upper 210 and bladder member 224. Each of the insole member defines a heel cup for receiving the heel of the wearer's foot and is adapted to provide calcaneal support to the foot. In this respect, the three insole members preferably utilized in association with the shoe 200 each include heel cups of decreasing size to provide the necessary calcaneal support as the swelling of the ankle reduces during the rehabilitation process.

Referring now to FIG. 9, the shoe 200 of the present invention further comprises three (3) selectively tightenable fasting straps which are cooperatively engaged to the boot upper 210 and operable to compress the boot upper 210 when tightened to maintain the shoe 200 upon the wearer's foot. In the second embodiment, the shoe 200 includes an elongate lower strap 272 which extends over the toe portion 212 of the boot upper 210 and includes a proximal end rigidly secured to the medial side of the toe portion 212 and a distal end which is extended through the first loop member 208 and releasably secured to a central portion of the lower strap 272 via a fastening member 274.

In addition to the lower strap 272, the shoe 200 includes an elongate intermediate strap 276 which extends over the vamp portion 214 of the boot upper 210. The intermediate strap 276 defines a proximal end which is rigidly secured to the medial side of the vamp portion 276, and a distal end which is extended through an elongate opening 278 defined within a second loop member 280 attached to and extending forwardly along the lateral side panel portion 218 of the ankle portion 216. After being tightened, the distal end of the intermediate strap 276 is releasably secured to a central portion thereof via a fastening member 282.

The shoe 200 further comprises an elongate upper strap 284 which extends about the ankle portion 216 of the boot upper 210. The opposed ends of the upper strap 284 are extended through sleeves defined within the lateral and medial side panel portions 218, 220, and are releasably secured to each other via a fastening member 286.

When the foot of the wearer is inserted into the boot upper 210 of the shoe 200 and rested upon the base portion of the brace member therewithin, the tightening of the lower, intermediate and upper straps 272, 276, 284 causes the lateral and medial struts of the brace member to assume particular orientations relative the ankle of the wearer's foot, which are the same as those assumed by the lateral and medial struts 56, 60 of the brace member 50. The tightening of the lower, intermediate and upper straps 272, 276, 284 further serves to compress the boot upper 210 which causes the adjacent edges 222 to draw toward each other, thus maintaining the shoe 200 upon the foot of the wearer. Like the shoe 10, the shoe 200 will be provided to the wearer with the extension collar 238 already engaged to the ankle portion 216 of the boot upper 210 and the bladder member 224 positioned therein. Once the foot is properly positioned within the shoe 200, the tightening of the lower, intermediate and upper straps 272, 276, 284 will immediately cause the lateral and medial struts of the brace member to provide support to the ankle. Typically, the lower strap 272 will be tightened first, followed in succession by the intermediate strap 276 and the upper strap 284. Thereafter, the collar strap 266 extending about the extension collar 238 will be tightened to provide a snug fit between the extension collar 238 and the lower shin area of the wearer's foot. The hand-held pump 98 is then utilized to inflate the bladder 240 of the extension collar 238 and the outer chamber of the bladder member 224. In addition or as an alternative to inflating the outer chamber with air, the inner chamber of the bladder member 224 may be filled with hot or cold water or attached to the water pumping apparatus 100 in the aforementioned manner to circulate hot or cold water therethrough. The advantages attendant to the shoe 10 and its preferred method of use are as previously discussed with respect to the rehabilitative shoe 10.

Additional modifications and improvements of the present invention may also be apparent may also be apparent to those skilled in the art. Thus, the particular combination of parts described and illustrated herein is intended to represent only one embodiment of the invention, and is not intended to serve as limitations of alternative devices within the spirit and scope of the invention.

What is claimed is:

1. A post-operative, ankle-supporting, rehabilitative shoe wearable on a foot having a plantar surface, ankle, heel, shin, midfoot, lateral malleolus and medial malleolus, said shoe comprising:
   a sole member defining lateral and medial edges and a generally planar top surface having heel, toe and central portions;
   a boot attached to said sole member, said boot defining a toe portion, a vamp portion and an ankle portion surrounding the ankle, heel and lower shin of the wearer's foot when the foot is inserted into the boot upper, said ankle portion including lateral and medial side panel portions;
   a brace member attached to the top surface of said sole member, comprising:
   a base portion formed to suit the shape of and sized to extend substantially along the length of the plantar surface of the wearer's foot; and
   curved lateral and medial struts extending upwardly from said base portion; and
   an inflatable bladder member selectively insertable into the ankle portion of the boot, said bladder member being sized and configured to extend about the ankle and heel of the wearer's foot when the foot is inserted into the boot;
   said lateral strut being formed and oriented on the base portion so as to extend upwardly along the lateral aspect of the ankle and about the front of the lateral malleolus and subsequently along the lower lateral and frontal aspects of the shin when the foot is inserted into the boot and the boot tightened; and
   said medial strut being formed and oriented on the base portion so as to extend upwardly along the medial aspect of the ankle and about the back of the medial malleolus and subsequently along the lower medial aspect of the shin when the foot is inserted into the boot and the boot tightened.

2. The shoe of claim 1 wherein said bladder member defines independently inflatable inner and outer chambers, each of said chambers including an inlet valve port and an outlet valve port.

3. The shoe of claim 2 wherein said lateral side panel portion of the boot includes a first pair of apertures disposed therein to accommodate the inlet valve ports of the inner and outer chambers when the bladder member is inserted into the ankle portion and the medial side panel portion of the boot includes a second pair of apertures disposed therein to accommodate the outlet valve ports of the inner and outer chambers when the bladder member is inserted into the ankle portion.

4. The shoe of claim 2 wherein said bladder member includes at least one fastener patch attached thereto to maintain said bladder member in releasable engagement to said boot when inserted into the ankle portion thereof.

5. The shoe of claim 2 further in combination with a hand-held air pump for selectively inflating said outer chamber with air via said inlet valve port subsequent to the insertion of said bladder member and the wearer's foot into the boot.

6. The shoe of claim 2 further in combination with a water pumping apparatus for selectively infusing water into said inner chamber via said inlet valve port subsequent to the insertion of said bladder member and the wearer's foot into the boot.

7. The shoe of claim 6 wherein said water pumping apparatus is fluidly connectable to the inlet and outlet valve ports of said inner chamber and adapted to circulate water therethrough.

8. The shoe of claim 1 wherein said bladder member is fabricated from rubber.

9. The shoe of claim 1 further comprising an extension collar releasably attachable to the ankle portion of said boot for increasing the height of said ankle portion and the support provided to the ankle thereby.

10. The shoe of claim 9 wherein said extension collar includes a selectively inflatable air bladder therein.

11. The shoe of claim 9 wherein said extension collar includes an elongate fastener strip extending thereabout for releasably attaching said extension collar to the ankle portion of the boot.

12. The shoe of claim 11 wherein said extension collar further includes a pair of stabilization straps attached thereto in opposed relation, each of said stabilization straps being releasably attachable to a respective one of a pair of connector receiving members disposed on the lateral and medial side panel portions of the ankle portion.

13. The shoe of claim 9 wherein said extension collar further comprises an elongate upper strap which is extensible thereabout and selectively tightenable in a manner operable to maintain the extension collar in tight engagement to the lower shin of the wearer's foot.

14. The shoe of claim 1 further comprising at least one fastening strap cooperatively engaged to said boot, said fastening strap being selectively tightenable and operable to compress the boot when tightened to maintain the shoe upon the wearer's foot.

15. The shoe of claim 14 further including a mid-sole, comprising:
a planar portion attached to the upper surface of said sole mender and disposed between said sole member and the base portion of said brace member, said planar portion being sized to substantially cover the heel and central portions of said top surface;
a continuous flange formed partially about and extending upwardly from the planar portion, said flange extending about the heel portion of said top surface and having a first end extending along the lateral edge of the sole member to the toe portion of the top surface and a second end extending along the medial edge of the sole member to the central portion of the top surface;
first and second flange apertures disposed in side-by-side relation in the first end of the flange; and
a third flange aperture disposed in the second end of the flange.

16. The shoe of claim 15 wherein said boot is attached to said sole member in a manner wherein said lateral strut extends upwardly between said lateral side panel portion and said flange and said medial strut extends upwardly between said medial side panel portion and said flange.

17. The shoe of claim 16 wherein said lateral strut is attached to said lateral side panel portion and said medial strut is attached to said medial side panel portion.

18. The shoe of claim 15 wherein said boot is attached to said sole member in a manner wherein said lateral strut extends upwardly within said lateral side panel portion and said medial strut extends upwardly within said medial side panel portion.

19. The device of claim 15 wherein said at least one fastening strap comprises:
an elongate lower strap extending over the toe portion of the boot and having a first proximal end rigidly secured to said toe portion and a first distal end extending through said first flange aperture, said first distal end being releasably attachable to a first central portion of the lower strap; and
an elongate intermediate strap extending over the vamp portion of the boot and having a second proximal end rigidly secured Go the ankle portion and a second distal end extending through said third and second flange apertures, respectively, said second distal end being releasably attachable to a second central portion of the upper strap.

20. The shoe of claim 1 wherein said sole member defines a bottom surface having an outwardly bowed configuration.

21. A method for fabricating a post-operative, ankle supporting, rehabilitative shoe comprising the steps of:
attaching a mid-sole to a sole member, said mid-sole including a planar portion attached to said sole member and a continuous flange formed partially about and extending upwardly from the planar portion;
attaching a brace member to the planar portion of the mid-sole and a toe portion of the sole member, said brace member including a base portion sized to completely cover the-planar surface of the mid-sole and the toe portion of the sole member when attached thereto and curved lateral and medial struts extending upwardly from the base portion;
attaching a boot to the sole member in a manner wherein the lateral strut extends upwardly within a lateral side panel portion of the boot and said medial strut extends upwardly within a medial side panel portion of the boot; and
inserting an inflatable bladder member into the boot in a manner wherein said bladder member extends about the ankle and heel of the wearer's foot when the foot is inserted into the boot.

22. The method of claim 21 further comprising the step of inflating an outer chamber of the bladder member with air subsequent to the insertion of the bladder member and the wearer's foot into the boot.

23. The method of claim 21 further comprising the step of filling an inner chamber of the bladder member with water subsequent to the insertion of the bladder member and the wearer's foot into the boot upper.

24. The method of claim 21 further comprising the step of attaching an extension collar to an ankle portion of the boot.

25. A post-operative, ankle-supporting, rehabilitative shoe wearable on a foot having a plantar surface, ankle, heel, shin, midfoot, lateral malleolus and medial malleolus, said shoe comprising:
a sole member defining lateral and medial edges and a generally planar top surface having heel, toe and central portions;
a boot attached to said sole member, said boot defining a toe portion, a vamp portion and an ankle portion surrounding the ankle, heel and lower shin of the wearer's foot when the foot is inserted into the boot, said ankle portion including lateral and medial side panel portions;
a brace member attached to the top surface of said sole member, comprising:
a base portion formed to suit the shape of and sized to extend substantially along the length of the plantar surface of the wearer's foot; and
curved lateral and medial struts extending upwardly from said base portion; and an inflatable bladder member selectively insertable into the vamp and ankle portions of the boot, said bladder member being sized and configured to extend about the ankle and heel and over the midfoot of the wearer's foot when the foot is inserted into the boot;

said lateral strut being formed and oriented on the base portion so as to extend upwardly along the lateral aspect of the ankle and about the front of the lateral malleolus and subsequently along the lower lateral and frontal aspects of the shin when the foot is inserted into the boot and the boot tightened; and said medial strut being formed and oriented on the base portion so as to extend upwardly along the medial aspect of the ankle and about the back of the medial malleolus and subsequently along the lower medial aspect of the shin when the foot is inserted into the boot and the boot tightened.

26. The shoe of claim 25 wherein said bladder member defines independently inflatable inner and outer chambers, said inner chamber including an inlet valve port and an outlet valve port and said outer chamber including an inlet/outlet valve port.

27. The shoe of claim 26 further in combination with a hand-held air pump for selectively inflating said outer chamber with air via said inlet/outlet valve port subsequent to the insertion of said bladder member and the wearer's foot into the boot.

28. The shoe of claim 26 further in combination with the water pumping apparatus for selectively infusing water into said inner chamber via said inlet valve port subsequent to the insertion of said bladder member and the wearer's foot into the boot.

29. The shoe of claim 28 wherein said water pumping apparatus is fluidly connectable to the inlet and outlet valve ports of said inner chamber and adapted to circulate water therethrough, 30. The shoe of claim 25 wherein said bladder member is fabricated from rubber.

31. The shoe of claim 25 further comprising an extension collar releasably attachable to the ankle portion of said boot for increasing the height of said ankle portion and the support provided to the ankle thereby, 32. The shoe of claim 31 wherein said extension collar includes a selectively inflatable air bladder therein.

33. The shoe of claim 31 wherein said extension collar includes an elongate fastener strip extending thereabout for releasably attaching said extension collar to the ankle portion of the boot.

34. The shoe of claim 31 wherein said extension collar further comprises an elongate collar strap which is extensible thereabout and selectively tightenable in a manner operable to maintain the extension collar in tight engagement to the lower shin of the wearer's foot, 35. The shoe of claim 25 wherein said boot is attached to said sole member in a manner wherein said lateral strut extends upwardly within said lateral side panel portion and said medial strut extends upwardly within said medial side panel portion.

36. The shoe of claim 25 wherein said sole member defines a bottom surface having an outwardly bowed configuration.

37. The shoe of claim 25 further comprising at least one fastening strap cooperatively engaged to said boot, said fastening strap being selectively tightenable and operable to compress the boot when tightened to maintain the shoe upon the wearer's foot.

* * * * *